United States Patent
Katscher et al.

(10) Patent No.: US 11,353,532 B2
(45) Date of Patent: Jun. 7, 2022

(54) (3-N) DIMENSIONAL DETERMINATION OF ELECTRIC CONDUCTIVITY

(71) Applicant: KONINKLIJKE PHILIPS N.V., Eindhoven (NL)

(72) Inventors: Ulrich Katscher, Norderstedt (DE); Christian Findelkee, Norderstedt (DE); Jochen Keupp, Rosengarten (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/982,071

(22) PCT Filed: Mar. 11, 2019

(86) PCT No.: PCT/EP2019/055939
§ 371 (c)(1),
(2) Date: Sep. 18, 2020

(87) PCT Pub. No.: WO2019/179796
PCT Pub. Date: Sep. 26, 2019

(65) Prior Publication Data
US 2021/0072333 A1    Mar. 11, 2021

(30) Foreign Application Priority Data
Mar. 20, 2018 (EP) .................................. 18162709

(51) Int. Cl.
*G01V 3/00* (2006.01)
*G01R 33/54* (2006.01)
(Continued)

(52) U.S. Cl.
CPC ......... *G01R 33/543* (2013.01); *G01R 33/385* (2013.01); *G01R 33/54* (2013.01); *A61B 5/055* (2013.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 6,486,669 B1 * 11/2002 Sinkus ................... G01R 33/28
324/309
2006/0149217 A1 * 7/2006 Hartlep ................ A61B 5/4893
604/503
(Continued)

OTHER PUBLICATIONS

Katscher U et al., Elecliic properties tomography: Biochemical, physical and technical background, evaluation and clinical applications, NMR Biomedicine 30 (2017) e3729.
(Continued)

*Primary Examiner* — Walter L Lindsay, Jr.
*Assistant Examiner* — Frederick Wenderoth (57) ABSTRACT

The invention relates to a magnetic resonance imaging system (100) for determining an approximation (150) of an electric conductivity distribution within a three-dimensional anatomical structure of interest. The determining comprises acquiring a first set of (3-n)-dimensional magnetic resonance data (144), reconstructing a (3-n)-dimensional phase distribution (146) using the (3-n)-dimensional magnetic resonance data (144), calculating a (3-n)-dimensional electric conductivity distribution (148) using spatial derivatives within the (3-n) dimensions and applying to the (3-n)-dimensional electric conductivity distribution (148) a scaling factor compensating for the relative reduction of dimensions by n.

20 Claims, 4 Drawing Sheets

(51) Int. Cl.
  *G01R 33/385* (2006.01)
  *A61B 5/055* (2006.01)
(58) Field of Classification Search
  USPC .......................................................... 324/309
  See application file for complete search history.

(56) References Cited

U.S. PATENT DOCUMENTS

| | | | |
|---|---|---|---|
| 2010/0198101 | A1 | 8/2010 | Song et al. |
| 2012/0169333 | A1 | 7/2012 | Katscher et al. |
| 2012/0274783 | A1* | 11/2012 | Ko .......................... A61B 3/113 |
| | | | 348/169 |
| 2012/0306493 | A1 | 12/2012 | Voigt et al. |
| 2014/0239951 | A1 | 8/2014 | Van Lier et al. |
| 2016/0061921 | A1* | 3/2016 | Katscher ............ G01R 33/4828 |
| | | | 324/309 |
| 2016/0367141 | A1 | 12/2016 | Lee et al. |
| 2017/0030988 | A1 | 2/2017 | Stehning et al. |
| 2017/0239493 | A1* | 8/2017 | Vilsmeier ................ A61B 6/50 |
| 2017/0303813 | A1 | 10/2017 | Lattanzi et al. |

OTHER PUBLICATIONS

Kim SY et al., "Correlation between conductivity and prognostic factors in invasive breast cancer using MREPT", Eur Radiol. 26 (2016) 2317-2326.

Tha Khin Khin et al ., "Noninvasive electrical conductivity measurement by MRI: a test of its validity and the electrical conductivity characteristics of glioma", EurRad (2017).

D Gursoy et al.,"Reconstruction artefacts in magnetic induction tomography due to patient's movement during data acquisition" Physiol. Meas. 30 p. S165-S174 (2009).

Edmond Balidemaj et al. "Feasibility of Electric Property Tomography of Pelvic Tumors at 3T" Magnetic Resonance in Med. 73 p. 1505-1513 (2015).

Xiaotong Zhang et al., Complex B1 Mapping and Electrical Properties Imaging of the Human Brain Using a 16-channel Transceiver Coil at 7T; Magnetic Reson. in Med. 69 p. 1285-1296 (2013).

International Search Report and Written Opinion from PCT/EP2019/055939 dated Jun. 7, 2019.

Lee Seung-Kyun et al: "Measurement of electrical properties of biological tissue at radio frequencies using magnetic resonance imaging", 2015 9th European Conference on Antennas and Propagation (EUCAP), EURAAP, Apr. 13, 2015 (Apr. 13, 2015), pp. 1-4.

Hafalir Fatih S et al: "Convection-Reaction Equation Based Magnetic Resonance Electrical Properties Tomography (cr-MREPT)",IEEE Transactions on Medical Imaging, IEEE Service Center, Piscataway, NJ, US, vol. 33, No. 3, Mar. 1, 2014 (Mar. 1, 2014), pp. 777-793.

Jin Keun Seo et al: "Magnetic resonance electrical impedance tomography (MREIT): conductivity and current density imaging", Journal of Physics: Conference Series,Institute of Physics Publishing, Bristol,GB,vol. 12, No. 1,Jan. 1, 2005 (Jan. 1, 2005), pp. 140-155.

Woo E J ft al: "Conductivity images of biological tissue phantoms using a 3.0 tesla MREIT system", Proceedings of the 26th Annual International Conference of the IEEE EMBS San Francisco,CA, IEEE Service Center, Piscataway, NJ, vol. 3, Sep. 1, 2004.

\* cited by examiner

# (3-N) DIMENSIONAL DETERMINATION OF ELECTRIC CONDUCTIVITY

CROSS REFERENCE TO RELATED APPLICATIONS

This application is a U.S. national phase application of International Application No. PCT/EP2019/055939 filed on Mar. 11, 2019, which claims the benefit of EP Application Serial No. 18162709.2 filed on Mar. 20, 2018 and is incorporated herein by reference.

FIELD OF THE INVENTION

The invention relates to magnetic resonance imaging, in particular to determining of an electric conductivity using magnetic resonance imaging data.

BACKGROUND OF THE INVENTION

Electric Properties Tomography (EPT) is able to determine a patient's electric conductivity quantitatively in vivo by calculating the second derivative of the RF-related phase of a 3D MRI scan in all three spatial directions. EPT is for example described in the journal article by Katscher U et al.: "Electric properties tomography: Biochemical, physical and technical background, evaluation and clinical applications", NMR Biomedicine 2017; 30 (8): e3729.

In EPT a patient's electric properties like electric conductivity may be derived using standard magnetic resonance imaging (MRI) setups and standard MRI sequences. EPT does not require additional externally mounted electrodes, currents or radiofrequency (RF) probes. EPT is based on quantitative MRI, i.e. it yields absolute values of conductivity.

Clinical studies indicated that the electric conductivity measured with EPT is correlated with the malignancy of tumors, like e.g. of breast tumors and brain tumors. Thus, EPT may provide an approach to analyze in vivo the malignancy of tumors.

In the article "Measurement of electrical properties of biological tissue at radio frequencies using magnetic resonance imaging", 2015 9th European Conference on Antennas and Propagation (EUCAP), EURAAP, 13. April 2015, pages 1-4, Lee Seung-Kyun et al. describes a usage of image shading in high-field magnetic resonance imaging (MRI) due to radio-frequency (RF) wave propagation effects in biological tissue to measure the electrical conductivity and relative permittivity of tissue in vivo. A method is provided to extract electrical properties of biological tissue from RF-shaded MR images without an explicit RF field mapping.

SUMMARY OF THE INVENTION

Embodiments may have the beneficial effect of enabling a calculation of a suitable approximation of the 3D electric the invention provides for a magnetic resonance imaging system, a method of operating a magnetic resonance imaging system and a computer program product in the independent claims. Embodiments are given in the dependent claims.

In one aspect, the invention relates to a magnetic resonance imaging system. The magnetic resonance imaging system comprises a memory storing machine executable instructions and pulse sequence commands. The pulse sequence commands are configured for controlling the magnetic resonance imaging system to acquire magnetic resonance data from an imaging zone. Furthermore, the magnetic resonance imaging system comprises a processor. The processor is configured to execute the machine executable instructions. An execution of the machine executable instructions causes the processor to control the magnetic resonance imaging system to determine an approximation of an electric conductivity distribution within a three-dimensional anatomical structure of interest in the imaging zone.

The determining comprises acquiring a first set of (3-n)-dimensional magnetic resonance data using the pulse sequence commands, with n either being n=1 or n=2. Thus, the first set comprising at least one of the following: 2-dimensional magnetic resonance data of a first plane or 1-dimensional magnetic resonance data of a first line intersecting the anatomical structure of interest. Furthermore, a (3-n)-dimensional phase distribution is reconstructed using the (3-n)-dimensional magnetic resonance data. A (3-n)-dimensional electric conductivity distribution is calculated using spatial derivatives within the (3-n) dimensions and to the (3-n)-dimensional electric conductivity distribution a scaling factor compensating for the relative reduction of dimensions by n is applied.

Embodiments may have the beneficial effect of significantly reducing the time required for the acquisition of the MRI data. The acquisition of (3-n)-dimensional MRI data, i.e. MRI data of a sectional plane or of a sectional line through the imaging zone, may be significantly faster than an acquisition of 3-dimensional MRI data, i.e. MRI data of the full 3D imaging zone. The shorter acquisition time may enable acquiring motion artifact free MRI data at time scales which are shorter than the typical time a patient is able to hold his or her breath. The reduction of information, i.e. the reduction of dimensions in which MRI data is acquired, may be efficiently compensated using the scaling factor. Thus, a realistic approximation of the electrical conductivity of the anatomical structure of interest at selected points, i.e. points comprised by the intersecting plane or intersecting line, may be provided. Based on this approximation, e.g. the malignancy of tumor tissue intersected by the respective plane or line, may be analyzed and/or determined.

EPT measurements in the abdominal and thoracic area, e.g. for analyze in vivo the malignancy of tumors, have the basic problem, that they are hampered by respiratory motion. Motion, i.e. motion of subject from which MRI data is acquired, is a particular problem for EPT and may result in more severe disturbances than a simple signal blurring or ghosting as observed in standard MR imaging. Motion impacts the MRI phase, which is used to derive the electric conductivity. Motion induced phase components may spoil conductivity reconstruction in an unpredictable manner. Thus, the presence and impact of motion artifacts on the electric conductivity cannot be identified as easy as in case of a standard MRI intensity image. Additionally, the general need for 3D MRI data acquisitions in EPT prolongs scan durations, making EPT scans particularly prone to impact of motion. For example, a patient is able to hold his or her breath only for a quite limited amount of time. Compared with the scale of an average patient is able to hold his or her breath, the time required for a 3D MRI data acquisitions with sufficient resolution, i.e. to determine the electric conductivity of tumor tissue in vivo, is too long. In other words, it may in general not be able to acquire 3D MRI data with a sufficient resolution without spoiling the result due to motion caused by breathing.

Embodiments suggest a (3-n)-dimensional data acquisition with the results for the electric conductivity being scaled up in order to compensate for the reduced number of dimensions resolved by the (3-n)-dimensional data acquisition compared to the required 3-dimensional data. This approach is also referred to as "Conductivity Weighted Imaging" (CWI) herein. The (3-n)-dimensional data acquisition may comprise a 2-dimensional and/or a 1-dimensional data acquisition.

Embodiments may thus comprise calculating second order derivatives of the phase provided by 2D MRI data. The 2D MRI data correspond to a plane through imaging volume. The derivatives are calculated along the two spatial coordinates in-plane, i.e. the two spatial coordinates which span the respective imaging plane. The derivatives of the phase may result in a 2D electric conductivity which may be used for approximating the 3D electric conductivity using a scaling factor to compensate for the reduced number of dimensions taken into account. This scaling factor may be estimated to yield roughly three halves, assuming that in first order approximation each spatial direction contributes equally to the total 3D electric conductivity resulting in a 2D electric conductivity of roughly two thirds of the 3D electric conductivity.

According to alternative embodiments, 1D MRI data may be acquired along a line, i.e. 1D pencil beam. The second order derivative of the phase along line, i.e. along the spatial coordinate in which the line extends, provides a 1D electric conductivity which may be used for approximating the 3D electric conductivity using a scaling factor to compensate for the reduced number of dimensions. The scaling factor may roughly yield three assuming that in first order approximation each spatial direction contributes equally to the total 3D electric conductivity. The 1D electric conductivity may thus be assumed as one third of the 3D electric conductivity.

conductivity using 1D and/or 2D MRI data. 1D and 2D MRI data may be acquired significantly faster than 3D MRI data. Thus, embodiments may shorten the time of the EPT scan such that the scan may be performed in a single breath-hold. The EPT scan may even be performed during free breathing assuming that the time scale required for the scan is short enough such that the motion during that time is negligible.

Embodiments may thus allow to use EPT even in the abdominal and thoracic area which may strongly be influenced by breathing motion. Thus, the usage of EPT-based tumor conductivity analysis may be extended to the abdominal and thoracic area. According to embodiments the orientation of the scan geometry, i.e. plane or line, may be chosen according to the spatial trajectory of the tumor during a breathing cycle, i.e. the plane or line may extend along the trajectory in order to maximize the fraction of the tumor trajectory, which is covered by the chosen 1D or 2D scan geometry. This may in particular be advantages, if only a single 1D/2D scan is/can be executed.

Embodiments may be applied to estimate conductivity of ROIs suffering e.g. breathing motion. This may predominantly applicable for lung and liver tumors. Without taking breath-hold into account, embodiments may also be applied for gastrointestinal motion, like e.g., colon/rectal cancer.

According to embodiments, the scaling factor is determined assuming that within the three-dimensional anatomical structure of interest each of the three dimensions contributes equally to the electric conductivity distribution to be approximated.

Embodiments may have the beneficial effect that an efficient compensation for the reduced amount of information taken into account may be implemented. Thus, to obtain an estimation of the actual quantitative conductivity value of the 3-dimensional anatomical structure of interest, e.g. a scaling factor of 3/2=1.5 (2D) or 3 (1D) maybe taken into account.

According to Maxwell's equations, electric conductivity $\sigma$ may be calculated from the image "transceive" phase $\phi$ via the (simplified) Helmholtz equation $$\sigma = (\partial_x^2 \phi + \partial_y^2 \phi + \partial_z^2 \phi)/(2\omega\mu_0)$$

with $\omega$ being the Larmor frequency and $\mu_0$ the vacuum permeability. The Helmholtz equation assumes that electric properties as well as the B1-magnitude are sufficiently constant locally. Since the anatomical structures of interest which are analyzed using EPT are 3D structures, the electric conductivity within such structures depends on derivatives along each of the three spatial coordinates, i.e. x, y, and z. Embodiments may further utilize the approximation $$\partial_x^2 \phi \approx \partial_y^2 \phi \approx \partial_z^2 \phi$$

such that the Helmholtz equation becomes $$\sigma = 3/2(\partial_u^2 \phi + \partial_v^2 \phi)/(2\omega\mu_0)$$

in case of 2D MRI data with u, v being the two spatial in-plane coordinates of the 2D MRI dataset, or $$\sigma = 3\partial_r^2 \phi /(2\omega\mu_0)$$

in case of 1D MRI data with r being the spatial coordinate along a 1D line. With the 2D and 1D approximation equations provided above, it may be possible to estimate electric conductivity from short scans, which may suffer significantly less from motion artefacts than lengthy 3D scans traditionally required for EPT.

According to embodiments, the 1D/2D MRI scans may be repeated with different orientations of the plane/line from which the (3-n)-dimensional MRI data is acquired. The additional orientations may e.g. be chosen orthogonal to the original scan geometry to simplify further derivatives and to reduce correlations between the directions along which the derivatives are calculated. The different scans may be measured as separate scans or in an interleaved manner, i.e. successively with the order of the orientations repeating.

If at least three, e.g. interleaved, 1D scans relate to the same motion state and intersect each other in a common voxel, an exact EPT reconstruction may be enabled for the common voxel at the crossing of the different lines. The exact value for the electric conductivity, i.e. $\sigma_{exact}$, at the common voxel may be provided by the sum of the three different 1-dimensional electric conductivity values, i.e. $\sigma_{1D, i}$ with i=x, y, z, calculated at the same voxel for the three different lines. Using a ratio between $\sigma_{exact}$ and one of the $\sigma_{1D, i}$ with i=x, y, z, or between $\sigma_{exact}$ and an average value of the three $\sigma_{1D, i}$ with i=x, y, z, the scaling factor may be calculated taking different contribution for different directions.

If at least two, e.g. interleaved, 2D scans 1 and 2 relate to the same motion state and intersect each other in a common voxel along a line of common voxels, an exact EPT reconstruction may be enabled for each of the common voxels at the crossing line of the different planes. Analogous to the 1D case above, a scaling factor may be calculated for each of the voxels, e.g. using a ratio between $\sigma_{exact}$ at the respective voxel and a 2-dimensional electric conductivity values $\sigma_{2D, i}$ with i=1, 2 of one of the planes 1 and 2 or between $\sigma_{exact}$ and an average value of the two $\sigma_{2D, i}$ with i=1, 2. In this case, $\sigma_{exact}$ may e.g. be calculated using one of the 2-dimensional electric conductivity values $\sigma_{2D, i}$ with i=1, 2 and a 1-dimensional electric conductivity values, i.e. $\sigma_{1D}$, for an orthogonal direction provided by the second one of the two planes. In addition, the values calculated for the scaling factor at the common voxels along the crossing line may be averaged to improve the result for the scaling factor.

According to embodiments, the determining of the approximation of the electric conductivity distribution is repeated for a second and a third line intersecting the first line in a common point within the anatomical structure of interest.

Embodiments may have the beneficial effect that they provide electric conductivity distribution in different directions and may allow for calculating an exact or at least more accurately approximated value for the electric conductivity of the anatomical structure of interest at the common point, i.e. at the voxel representing the common point. The respective value may be used for calculating a scaling factor.

According to embodiments, the first, second and third line extend perpendicularly relative to each other. Embodiments may have the beneficial effect that they may allow for calculating an exact value for the electric conductivity of the anatomical structure of interest at the common point. The respective value may be used for calculating a scaling factor.

According to embodiments, the determination of the approximation of the electric conductivity distribution is repeated for a second plane intersecting the first plane within the anatomical structure of interest.

Embodiments may have the beneficial effect that they provide electric conductivity distribution in different directions and may allow for calculating an exact or at least more accurately approximated value for the electric conductivity of the anatomical structure of interest along the intersection line of the two planes, i.e. at the voxel representing the respective intersection line. The respective values may be averaged and used for calculating a scaling factor.

According to embodiments, the second plane extends perpendicularly relative to the first plane. Embodiments may have the beneficial effect that they may allow for calculating an exact value for the electric conductivity of the anatomical structure of interest along the intersection line. The respective value may be used for calculating a scaling factor.

According to embodiments, the determination of the approximation of the electric conductivity distribution is repeated for a third plane intersecting the first and second plane in a common point within the anatomical structure of interest. Embodiments may have the beneficial effect that a larger number of approximated values and/or exact values for the electric conductivity of the anatomical structure of interest may be provided. In particular exact values may not only be provided along one intersection line, but along three intersection lines crossing each other.

According to embodiments, the third plane extends perpendicularly relative to the first and second plane. Embodiments may have the beneficial effect of providing exact values not only along one intersection line, but along three intersection lines crossing each other perpendicularly. Thus, exact values may be provided in each spatial direction x, y, z.

According to embodiments, the determination of the approximation of the electric conductivity distribution is repeated for a fourth line intersecting the first plane within the anatomical structure of interest. Embodiments may have the beneficial effect that data acquisition for a line may be faster than for a plane. Thus, having a cross-sectional distribution of the electric conductivity adding a line, a singular exact value of the electric conductivity of the anatomical structure of interest may be obtained.

According to embodiments, the fourth line extends perpendicularly relative to the first plane.

According to embodiments, the first set of (3-n)-dimensional magnetic resonance data is an averaged set of (3-n)-dimensional magnetic resonance data resulting from averaging over a plurality of second sets of (3-n)-dimensional magnetic resonance data acquired using the pulse sequence commands. Embodiments may have the beneficial effect that using averaged (3-n)-dimensional magnetic resonance data SNR may be improved. However, acquiring plurality of second sets of MRI data may only be possible due to a reduction of acquisition time for each of the data acquisition. This reduction is the result of taking into account (3-n)-dimensional magnetic resonance data instead of 3-dimensional magnetic resonance data.

According to embodiments, each of the second sets of (3-n)-dimensional magnetic resonance data is checked for artifacts and only second sets data determined to be free of artifacts are used for the averaging. Embodiments may have the beneficial effect of providing reliable results for the electric conductivity. The presence of artifacts may e.g. be determined using additional (3-n)-dimensional MRI intensity images reconstructed from the (3-n)-dimensional magnetic resonance data. In case of n=1, a 2-dimensional MRI intensity images may be provided which may also be referred to as a 2-dimensional MRI intensity distribution. In case of n=2, a 1-dimensional MRI intensity image may be provided which may also be referred to as a 1-dimensional MRI intensity distribution. This 1-dimensional MRI intensity distribution may e.g. be represented in form of a graph.

According to embodiments, for each of the second sets of (3-n)-dimensional magnetic resonance data a position of the anatomical structure of interest is determined. In case the position of the anatomical structure of interest for one of the second sets is determined to be displaced relative to a reference position, one of the following is executed: the respective second set is discarded or the respective second set is registered with a reference set of (3-n)-dimensional magnetic resonance data representing the reference position of the anatomical structure of interest.

Embodiments may have the beneficial effect that a reduction of the equality of the approximation due to a changing position may be avoided. In particular it may effectively be prevented to combine components of the electric conductivity from different parts of the anatomical structure of interest.

According to embodiments, the short 1D or 2D MRI scans may be repeated in a dynamic series, which is e.g. started with the beginning of a breath-hold of the patient. The patient may be asked to hold his or her breath as long as it is comfortable. The dynamic scan series may be stopped when the patient starts breathing again. Different dynamics, i.e. MRI data sets acquired during breath-holding, may be averaged a posteriori according to the motion state of the respective MRI data set. Averaging over different dynamics may result in an improved signal-to-noise ratio.

The generation of the phase distribution may comprise a reconstruction of an MRI phase image using the acquired MRI data. The reconstruction may comprise a Fourier transformation of the acquired MRI data from k-space to image space. The resulting phase images and thus the underlying MRI datasets may be used to sort different sets of MRI data of the dynamic series into three groups:

Target group: these sets of MRI data represent the anatomical structure of interest, e.g. a tumor, without motion artefacts at a reference location during breath-hold. The reference location may e.g. be the position at beginning of the breath holding. Sets of MRI data of this group can be averaged to increase SNR.

Displacement group: these sets of MRI data represent the anatomical structure of interest, e.g. a tumor, without motion artefacts at a location which differs from the reference breath-hold's location. They may e.g. be acquired after the breath-hold in a suitable respiratory motion state. Sets of MRI data from this group may either be discarded or registered to the sets of MRI data of the target group for averaging to further increase SNR.

Corrupted group: these sets of MRI data represent motion artefacts, i.e. the anatomical structure of interest moved during acquisition, and may be discarded.

Averaging sets of MRI data from the target group and potentially also the displacement group may be performed before or after conductivity reconstruction. In other words, either the sets of MRI data may be averaged, the phase distributions generated from the sets of MRI data may be averaged or the results for the electric conductivity may be averaged.

In another aspect, the invention relates to a method of operating a magnetic resonance imaging system. The magnetic resonance imaging system comprises a memory storing machine executable instructions and pulse sequence commands. The pulse sequence commands are configured for controlling the magnetic resonance imaging system to acquire magnetic resonance data from an imaging zone. The magnetic resonance imaging system furthermore comprises a processor. An execution of the machine executable instructions by the processor causes the processor to control the magnetic resonance imaging system according to the method. The method comprises determining an approximation of an electric conductivity distribution within a three-dimensional anatomical structure of interest in the imaging zone.

The determining comprises acquiring a first set of (3-n)-dimensional magnetic resonance data using the pulse sequence commands, with n either being n=1 or n=2. Thus, the first set comprising at least one of the following: 2-dimensional magnetic resonance data of a first plane or 1-dimensional magnetic resonance data of a first line intersecting the anatomical structure of interest. Furthermore, a (3-n)-dimensional phase distribution is reconstructed using the (3-n)-dimensional magnetic resonance data. A (3-n)-dimensional electric conductivity distribution is calculated using spatial derivatives within the (3-n) dimensions and to the (3-n)-dimensional electric conductivity distribution a scaling factor compensating for the relative reduction of dimensions by n is applied.

In another aspect, the invention relates to a computer program product comprising machine executable instructions for execution by a processor controlling a magnetic resonance imaging system using pulse sequence commands. The pulse sequence commands are configured for controlling the magnetic resonance imaging system to acquire magnetic resonance data from an imaging zone. An execution of the machine executable instructions causes the processor to control the magnetic resonance imaging system to determine an approximation of an electric conductivity distribution within a three-dimensional anatomical structure of interest in the imaging zone.

The determining comprises acquiring a first set of (3-n)-dimensional magnetic resonance data using the pulse sequence commands, with n either being n=1 or n=2. Thus, the first set comprising at least one of the following: 2-dimensional magnetic resonance data of a first plane or 1-dimensional magnetic resonance data of a first line intersecting the anatomical structure of interest. Furthermore, a (3-n)-dimensional phase distribution is reconstructed using the (3-n)-dimensional magnetic resonance data. A (3-n)-dimensional electric conductivity distribution is calculated using spatial derivatives within the (3-n) dimensions and to the (3-n)-dimensional electric conductivity distribution a scaling factor compensating for the relative reduction of dimensions by n is applied.

The aforementioned embodiments of the invention may enable to calculate a reasonable approximation for values of an electric conductivity within an anatomical structure of interest. For this purpose, (3-n)-dimensional magnetic resonance data is acquired. Due to the reduction of dimensions, the acquisition may be speeded up significantly. Reconstructing a (3-n)-dimensional phase distribution, a (3-n)-dimensional electric conductivity distribution may be calculated and used for approximating the exact electric conductivity distribution within the 3-dimensional anatomical structure of interest. The reduced number of dimensions and the resulting loss of information may be compensated by applying a scaling factor.

The reduced acquisition time may allow to acquire several sets of (3-n)-dimensional magnetic resonance data for the same or different spatial directions. This may be used to improve SNR, to calculate exact values for the electric conductivity distribution at individual points and/or to improve the calculation of the scaling factor.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and/or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) imaging data is defined herein as being the recorded measurements of radio frequency signals emitted by nuclear spins using the antenna of a magnetic resonance imaging system during a magnetic resonance imaging scan. A Magnetic Resonance Imaging (MRI) image or MR image is defined herein as being the reconstructed two or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
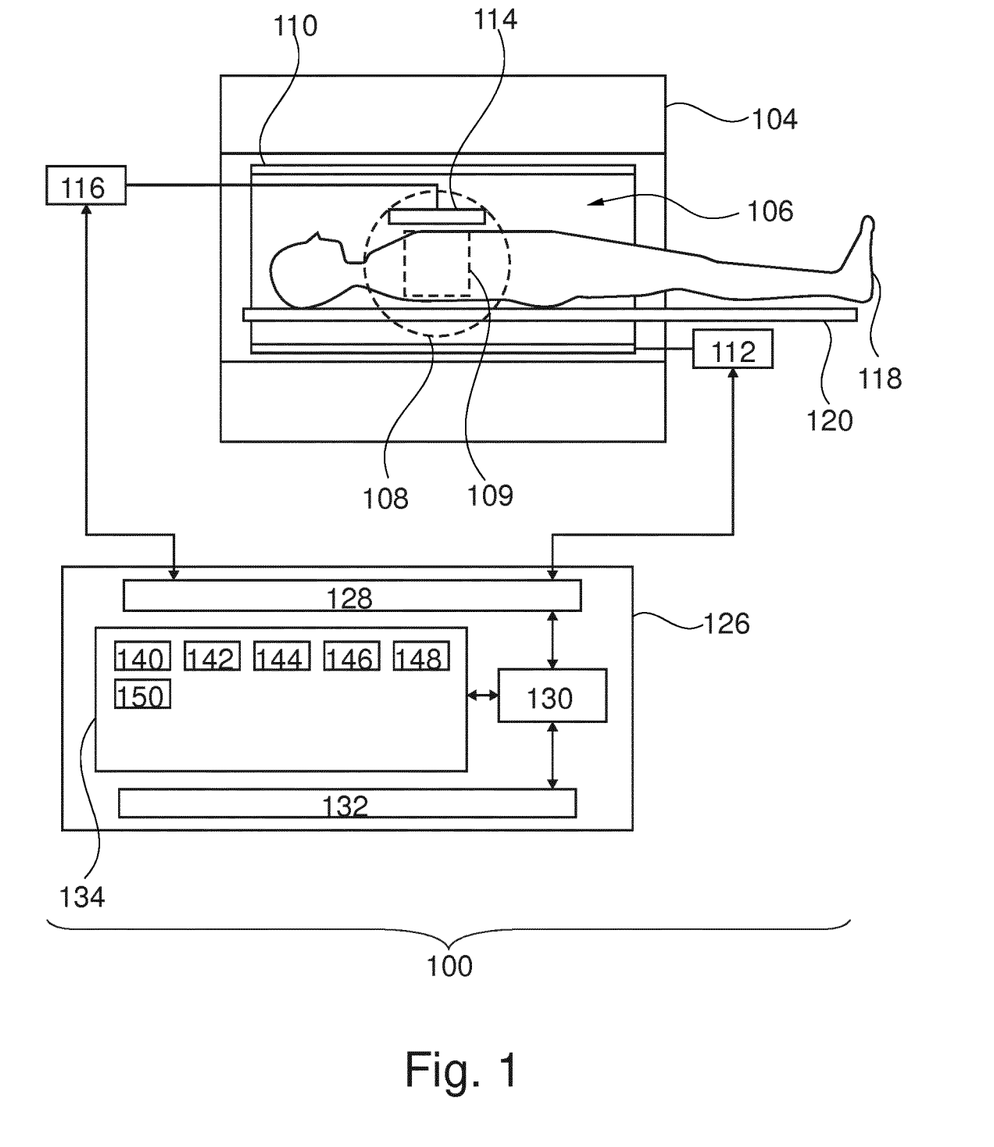
FIG. 1 shows an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible. For instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance data is typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise, the transceiver 116 may also represent a separate transmitter and separate receivers. The radio-frequency coil 114 may also have multiple receive/transmit elements and the radio frequency transceiver 116 may have multiple receive/transmit channels. For example, if a parallel imaging technique such as SENSE is performed, the radio-frequency coil 114 will have multiple coil elements.

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium. The user interface 132 may comprise a display for displaying results of a data acquisition and/or processing executed by the magnetic resonance imaging system 100.

The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions. The computer memory 134 is further shown as containing pulse sequence commands 142.

The pulse sequence commands 142 are configured for controlling the magnetic resonance imaging system 100 to acquire a set of (3-n)-dimensional magnetic resonance data 144, with n=1 or n=2. The machine-executable instructions 140 may enable the processor 130 to reconstruct a (3-n)-dimensional phase distribution 146 using the set of (3-n)- dimensional magnetic resonance data 144. The machine-executable instructions 140 may enable the processor 130 to calculate a (3-n)-dimensional electric conductivity distribution 148 using the (3-n)-dimensional phase distribution 146. By applying a scaling factor compensating for the relative reduction of dimensions in the (3-n)-dimensional magnetic resonance data 144 to the (3-n)-dimensional electric conductivity distribution 148, an approximation of an electric conductivity distribution 150 within a 3-dimensional anatomical structure of interest in the imaging zone 108 may be obtained.

Figure 2A:
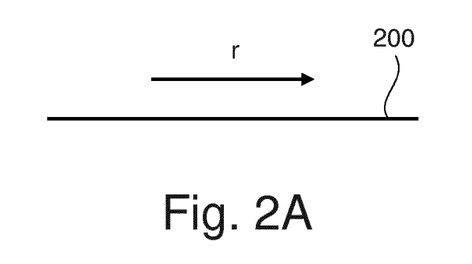
FIG. 2 illustrate different orientations and dimensions of data acquisition.

FIGS. 2A to 2F illustrate different exemplary orientations and dimensions for the (3-n)-dimensional magnetic resonance data acquisition. FIG. 2A shows an exemplary set of 1-dimensional magnetic resonance data in form of a first line 200 extending along the direction r. This set of 1-dimensional magnetic resonance data may be used to reconstruct a 1-dimensional phase distribution along the direction r. A 1-dimensional electric conductivity distribution may be calculated using spatial derivatives along the direction r, i.e.

$$\sigma = f_s \partial_r^2 \varphi / (2\omega\mu_0)$$

with a scaling factor $f_s = 3$ under the assumption that the derivatives in each spatial direction are approximately equal.

Figure 2B:
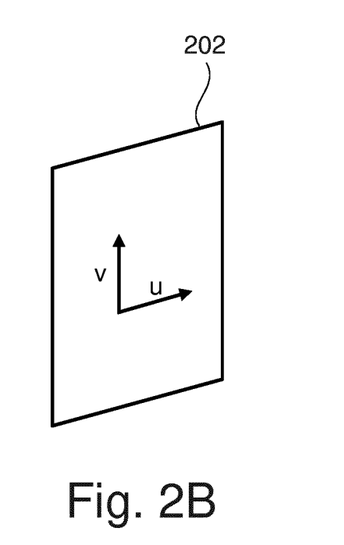

FIG. 2B shows an exemplary set of 2-dimensional magnetic resonance data in form of a first plane 202 extending along the directions u and v. This set of 2-dimensional magnetic resonance data may be used to reconstruct a 2-dimensional phase distribution along the directions u and v. A 2-dimensional electric conductivity distribution may be calculated using spatial derivatives along the directions u and v, i.e.

$$\sigma = f_s (\partial_u^2 \varphi + \partial_v^2 \varphi) / (2\omega\mu_0)$$

with a scaling factor $f_s = 3/2$ under the assumption that the derivatives in each spatial direction are approximately equal.

Figure 2C:
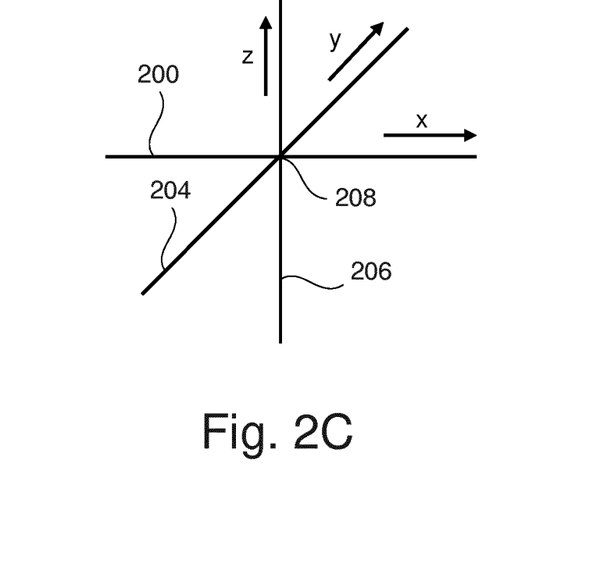

FIG. 2C shows three exemplary sets of 1-dimensional magnetic resonance data in form of three lines 200, 204, 206 which intersect perpendicularly in a common point 208. With three perpendicularly intersecting lines 200, 204, 206, derivatives may be calculated for each spatial direction x, y, z in the common point 208. Thus, the exact value of the electric conductivity may be determined at the common point 208. The remaining points along the lines 200, 204, 206 provide 1-dimensional electric conductivities as shown in FIG. 2A. The exact value of the electric conductivity at the common point 208 may be used to calculate a more realistic scaling factor.

Figure 2D:
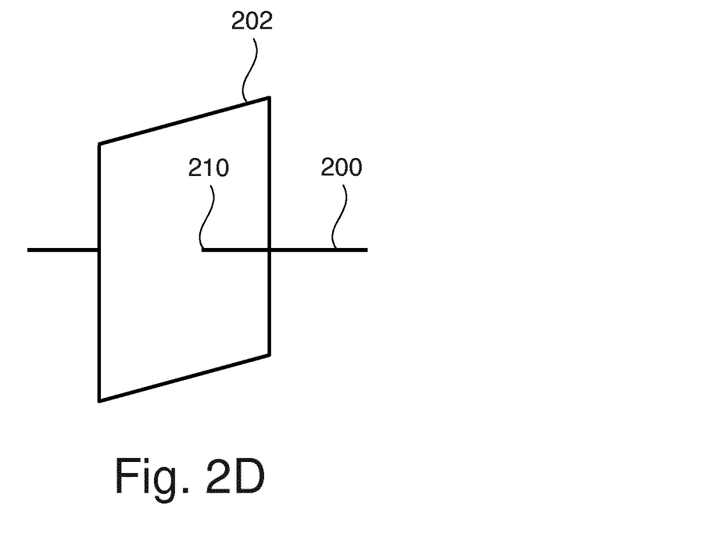

FIG. 2D shows 2-dimensional magnetic resonance data in form of a plane 202 intersected perpendicularly by a line 209 in a common point 210. The exact value of the electric conductivity may be determined at the common point 210, while the remaining points within the plane 202 and along the line 209 provide 2-dimensional and 1-dimensional electric conductivities as shown in FIG. 2B and FIG. 2A, respectively. The exact value of the electric conductivity at the common point 210 may be used to calculate a more realistic scaling factor.

Figure 2E:
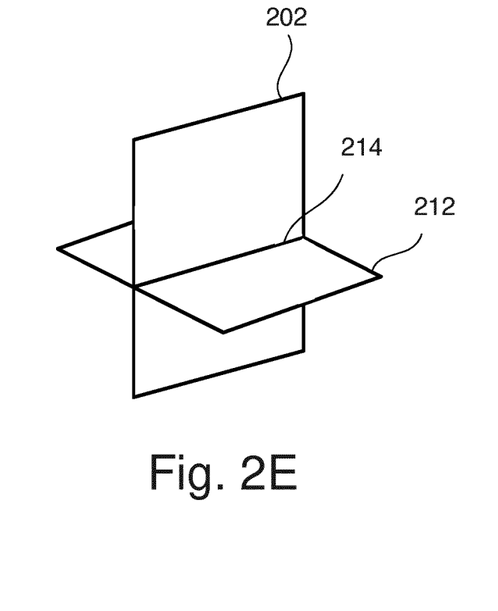

FIG. 2C shows two exemplary sets of 2-dimensional magnetic resonance data in form of two planes 202, 212 which intersect perpendicularly along a common line 214. With two perpendicularly intersecting planes 202, 212, derivatives may be calculated for each spatial direction x, y, z along the common line 214. Thus, the exact values of the electric conductivity may be determined at the point comprised by the common line 214. The remaining points within the planes 202, 212 provide 2-dimensional electric conductivities as shown in FIG. 2B. The exact values of the electric conductivity at the point comprised by the common line 214 may be used to calculate a more realistic scaling factor.

Figure 2F:
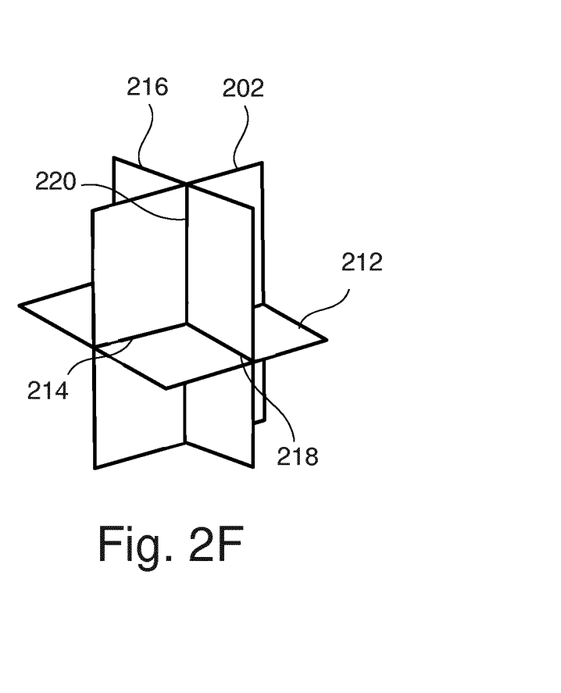

FIG. 2C shows three exemplary sets of 2-dimensional magnetic resonance data in form of three planes 200, 212, 216 which intersect perpendicularly in three lines 214, 218, 220, each common to two of the three planes 200, 212, 216. With three perpendicularly intersecting planes 200, 212, 216, derivatives may be calculated for each spatial direction x, y, z along the common lines 214, 218, 220. Thus, the exact value of the electric conductivity may be determined at points comprised by the common lines 214, 218, 220. The remaining points along the planes 200, 212, 216 provide 2-dimensional electric conductivities as shown in FIG. 2B. The exact value of the electric conductivity at points along the common lines 214, 218, 220 may be used to calculate a more realistic scaling factor.

Figure 3:
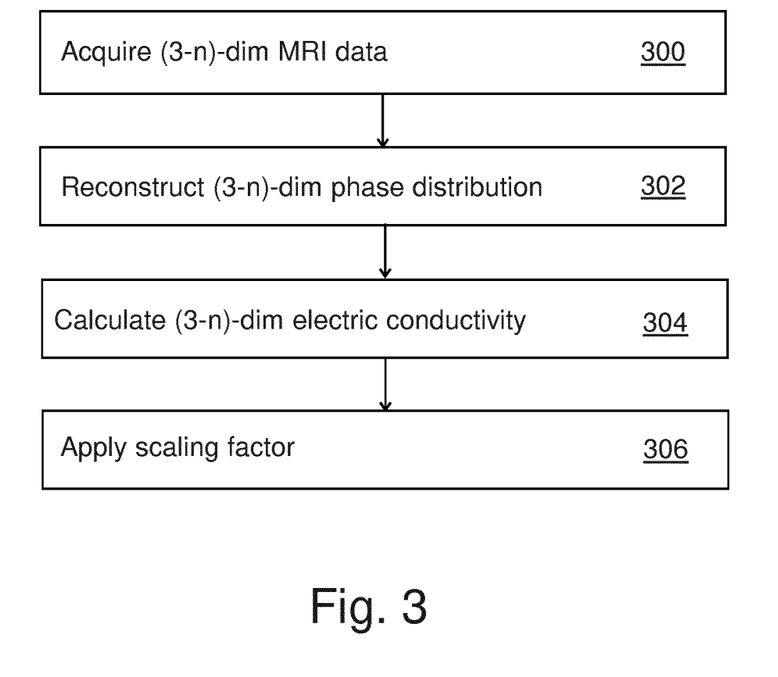
FIG. 3 illustrates an exemplary method of determining the electric conductivity.

FIG. 3 shows a flowchart which illustrates a method of operating the magnetic resonance imaging system 100 of FIG. 1 for determining an approximation of an electric conductivity distribution within a three-dimensional anatomical structure of interest in the imaging zone. In step 300, a set of (3-n)-dimensional magnetic resonance data is acquired with n either being n=1 or n=2. Thus, the first set may e.g. comprise 2-dimensional magnetic resonance data of a plane (cf. FIG. 2B) or 1-dimensional magnetic resonance data of line (cf. FIG. 2A). In step 302, a (3-n)-dimensional phase distribution is reconstructed using the (3-n)-dimensional magnetic resonance data acquired in step 300. In step 304, a (3-n)-dimensional electric conductivity distribution is calculated using spatial derivatives within the (3-n) dimensions. In step 306, a scaling factor compensating for the relative reduction of dimensions by n is applied. The scaling factor may be applied to the result of step 304 or alternatively to the (3-n)-dimensional phase distribution before calculating the derivatives.

Step 300 may be repeated for the same plane/line and an average of the (3-n)-dimensional magnetic resonance data over the resulting sets may be calculated in order to improve SNR. Furthermore or alternatively, the full method of determining the approximation of the electric conductivity distribution within the three-dimensional anatomical structure of interest in the imaging zone may be repeated several times with different orientations of the plane/line (cf. FIG. 2C to 2F). The repetition with different orientation may e.g. be executed in an interleaved fashion, i.e. orientation1, orientation2, orientation3, orientation1, orientation2, orientation3, orientation1, orientation2, orientation3, . . . , until e.g. the patient is not able to hold his or her breath any longer.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium

LIST OF REFERENCE NUMERALS

- 100 magnetic resonance imaging system
- 104 magnet
- 106 bore of magnet
- 108 imaging zone
- 109 region of interest
- 110 magnetic field gradient coils
- 112 magnetic field gradient coil power supply
- 114 radio-frequency coil
- 116 transceiver
- 118 subject
- 120 subject support
- 126 computer system
- 128 hardware interface
- 130 processor
- 132 user interface
- 134 computer memory
- 140 machine executable instructions
- 142 pulse sequence commands
- 144 (3-n)-dimensional magnetic resonance data
- 146 (3-n)-dimensional phase distribution
- 148 (3-n)-dimensional electric conductivity distribution
- 150 approximation of electric conductivity distribution
- 200 first line
- 202 first plane
- 204 second line
- 206 third line
- 208 common point
- 209 fourth line
- 210 common point
- 212 second plane
- 214 first common line
- 216 third plane
- 218 second common line
- 220 third common line

The invention claimed is:

1. A magnetic resonance imaging system, the magnetic resonance imaging system comprising:
- a memory storing machine executable instructions and pulse sequence commands, wherein the pulse sequence commands are configured for controlling the magnetic resonance imaging system to acquire magnetic resonance data from an imaging zone,
- a processor, wherein an execution of the machine executable instructions causes the processor to control the magnetic resonance imaging system to determine an approximation of an electric conductivity distribution within a three-dimensional anatomical structure of interest in the imaging zone, wherein the determining comprises:
- acquiring a first set of (3-n)-dimensional magnetic resonance data wherein n=1 or n=2, using the pulse sequence commands, the first set comprising at least one of the following:
  - 2-dimensional magnetic resonance data of a first plane or 1-dimensional magnetic resonance data of a first line intersecting the anatomical structure of interest;
- reconstructing a (3-n)-dimensional phase distribution using the (3-n)-dimensional magnetic resonance data;
- calculating a (3-n)-dimensional electric conductivity distribution using spatial derivatives within the (3-n) dimensions and applying to the (3-n)-dimensional electric conductivity distribution a scaling factor compensating for the relative reduction of dimensions by n.

2. A method of operating a magnetic resonance imaging system, the magnetic resonance imaging system comprising:
- a memory storing machine executable instructions and pulse sequence commands, wherein the pulse sequence commands are configured for controlling the magnetic resonance imaging system to acquire magnetic resonance data from an imaging zone,
- a processor, wherein an execution of the machine executable instructions causes the processor to control the magnetic resonance imaging system according to the method,
- wherein the method comprises determining an approximation of an electric conductivity distribution within a three-dimensional anatomical structure of interest in the imaging zone, wherein the determining comprises:
- acquiring a first set of (3-n)-dimensional magnetic resonance data wherein n=1 or n=2, using the pulse sequence commands, the first set comprising at least one of the following:
  - 2-dimensional magnetic resonance data of a first plane or 1-dimensional magnetic resonance data of a first line intersecting the anatomical structure of interest;
- reconstructing a (3-n)-dimensional phase distribution using the (3-n)-dimensional magnetic resonance data;
- calculating a (3-n)-dimensional electric conductivity distribution using spatial derivatives within the (3-n) dimensions and applying to the (3-n)-dimensional electric conductivity distribution a scaling factor compensating for the relative reduction of dimensions by n.

3. A computer program product comprising machine executable instructions stored on a non-transitory computer readable medium for execution by a processor to control a magnetic resonance imaging system using pulse sequence commands, wherein the pulse sequence commands are configured for controlling the magnetic resonance imaging system to acquire magnetic resonance data from an imaging zone,
- wherein an execution of the machine executable instructions causes the processor to control the magnetic resonance imaging system to determine an approximation of an electric conductivity distribution within a three-dimensional anatomical structure of interest in the imaging zone, wherein the determining comprises:
- acquiring a first set of (3-n)-dimensional magnetic resonance data using the pulse sequence commands, the first set comprising at least one of the following:
  - 2-dimensional magnetic resonance data of a first plane or 1-dimensional magnetic resonance data of a first line intersecting the anatomical structure of interest;
- reconstructing a (3-n)-dimensional phase distribution wherein n=1 or n=2, using the (3-n)-dimensional magnetic resonance data;
- calculating a (3-n)-dimensional electric conductivity distribution using spatial derivatives within the (3-n) dimensions and applying to the (3-n)-dimensional electric conductivity distribution a scaling factor compensating for the relative reduction of dimensions by n.

4. The magnetic resonance imaging system of claim 1, wherein the scaling factor is determined assuming that within the three-dimensional anatomical structure of interest each of the three dimensions contributes equally to the electric conductivity distribution to be approximated.

5. The magnetic resonance imaging system of claim 1, wherein the determining of the approximation of the electric conductivity distribution is repeated for a second and a third line intersecting the first line in a common point within the anatomical structure of interest.

6. The magnetic resonance imaging system of claim 5, wherein the first, second and third line extend perpendicularly relative to each other.

7. The magnetic resonance imaging system of claim 1, wherein the determination of the approximation of the electric conductivity distribution is repeated for a second plane intersecting the first plane within the anatomical structure of interest.

8. The magnetic resonance imaging system of claim 7, wherein the second plane extends perpendicularly relative to the first plane.

9. The magnetic resonance imaging system of claim 7, wherein the determination of the approximation of the electric conductivity distribution is repeated for a third plane intersecting the first and second plane in a common point within the anatomical structure of interest.

10. The magnetic resonance imaging system of claim 9, wherein the third plane extends perpendicularly relative to the first and second plane.

11. The magnetic resonance imaging system of claim 1, wherein the determination of the approximation of the electric conductivity distribution is repeated for a fourth line intersecting the first plane within the anatomical structure of interest.

12. The magnetic resonance imaging system of claim 1, wherein the fourth line extends perpendicularly relative to the first plane.

13. The magnetic resonance imaging system of claim 1, wherein the first set of (3-n)-dimensional magnetic resonance data is an averaged set of (3-n)-dimensional magnetic resonance data resulting from averaging over a plurality of second sets of (3-n)-dimensional magnetic resonance data acquired using the pulse sequence commands.

14. The magnetic resonance imaging system of claim 13, wherein each of the second sets of (3-n)-dimensional magnetic resonance data is checked for artifacts and only second sets data determined to be free of artifacts are used for the averaging.

15. The magnetic resonance imaging system of claim 14, wherein for each of the second sets of (3-n)-dimensional magnetic resonance data a position of the anatomical structure of interest is determined, in case the position of the anatomical structure of interest for one of the second sets is determined to be displaced relative to a reference position, one of the following is executed: the respective second set is discarded or the respective second set is registered with a reference set of (3-n)-dimensional magnetic resonance data representing the reference position of the anatomical structure of interest.

16. The computer program product of claim 3, wherein the determination of the approximation of the electric conductivity distribution is repeated for a fourth line intersecting the first plane within the anatomical structure of interest.

17. The computer program product of claim 16, wherein the fourth line extends perpendicularly relative to the first plane.

18. The computer program product of claim 3, wherein the first set of (3-n)-dimensional magnetic resonance data is an averaged set of (3-n)-dimensional magnetic resonance data resulting from averaging over a plurality of second sets of (3-n)-dimensional magnetic resonance data acquired using the pulse sequence commands.

19. The computer program product of claim 18, wherein each of the second sets of (3-n)-dimensional magnetic resonance data is checked for artifacts and only second sets data determined to be free of artifacts are used for the averaging.

20. The computer program product of claim 18, wherein for each of the second sets of (3-n)-dimensional magnetic resonance data a position of the anatomical structure of interest is determined, in case the position of the anatomical structure of interest for one of the second sets is determined to be displaced relative to a reference position, one of the following is executed: the respective second set is discarded or the respective second set is registered with a reference set of (3-n)-dimensional magnetic resonance data representing the reference position of the anatomical structure of interest.

* * * * *